(12) United States Patent
Modtland et al.

(10) Patent No.: US 8,901,335 B2
(45) Date of Patent: Dec. 2, 2014

(54) ORGANOMETALLIC COMPOUND PURIFICATION AND APPARATUS

(75) Inventors: Curtis D. Modtland, Lake Jackson, TX (US); Chet D. Davidson, Lake Jackson, TX (US)

(73) Assignee: Dow Global Technologies LLC, Midland, MI (US)

(*) Notice: Subject to any disclaimer, the term of this patent is extended or adjusted under 35 U.S.C. 154(b) by 165 days.

(21) Appl. No.: 13/549,401

(22) Filed: Jul. 13, 2012

(65) Prior Publication Data

US 2013/0184480 A1    Jul. 18, 2013

Related U.S. Application Data

(60) Provisional application No. 61/507,334, filed on Jul. 13, 2011.

(51) Int. Cl.
| | | |
|---|---|---|
| C07F 7/00 | (2006.01) | |
| C07F 5/06 | (2006.01) | |
| C07F 3/02 | (2006.01) | |
| C07F 5/00 | (2006.01) | |
| B01D 3/40 | (2006.01) | |
| C07B 63/00 | (2006.01) | |

(52) U.S. Cl.
CPC ... *C07F 5/00* (2013.01); *B01D 3/40* (2013.01); *C07F 3/02* (2013.01); *C07F 5/063* (2013.01); *C07F 5/064* (2013.01); *C07F 7/003* (2013.01); *C07B 63/00* (2013.01)
USPC ............. 556/51; 556/1; 556/81; 556/186; 556/187; 260/665 R

(58) Field of Classification Search
CPC ............. C07F 3/02; C07F 5/00; C07F 5/063; C07F 5/064; C07F 7/003; B01D 3/40; C07B 63/00
USPC ............... 556/1, 51, 81, 186, 187; 260/665 G
See application file for complete search history.

(56) References Cited

U.S. PATENT DOCUMENTS

| | | |
|---|---|---|
| 3,016,396 A | 1/1962 | Irie et al. |
| 4,251,453 A | 2/1981 | Garrison |
| 4,925,962 A | 5/1990 | Beard et al. |
| 4,948,906 A | 8/1990 | Beard |
| 5,951,820 A | 9/1999 | Ohsaki et al. |
| 6,495,707 B1 | 12/2002 | Leese et al. |
| 7,112,691 B2 | 9/2006 | Tsudera et al. |
| 7,166,734 B2 | 1/2007 | Shenai-Khatkhate et al. |

(Continued)

FOREIGN PATENT DOCUMENTS

| | | |
|---|---|---|
| CN | 1872861 A | 12/2006 |
| CN | 1872862 A | 12/2006 |

(Continued)

OTHER PUBLICATIONS

European Search Report of corresponding European Application No. 12 17 6093.

*Primary Examiner* — Porfirio Nazario Gonzalez
(74) *Attorney, Agent, or Firm* — S. Matthew Cairns

(57) ABSTRACT

A method of purifying crude organometallic compounds using a stripping column and a gas stream is provided. This method removes relatively more volatile impurities as compared to the organometallic compound.

12 Claims, 1 Drawing Sheet

(56) References Cited

U.S. PATENT DOCUMENTS

| | | |
|---|---|---|
| 7,179,931 B2 | 2/2007 | Tsudera et al. |
| 8,101,787 B2 | 1/2012 | Lipiecki et al. |
| 2013/0184481 A1* | 7/2013 | Modtland et al. ............... 556/70 |
| 2013/0211117 A1 | 8/2013 | Modtland et al. |
| 2013/0211118 A1 | 8/2013 | Modtland et al. |

FOREIGN PATENT DOCUMENTS

| | | |
|---|---|---|
| EP | 1 303 336 B1 | 9/2006 |
| JP | 3215195 | 7/2001 |
| WO | WO 97/40053 A1 | 10/1997 |

* cited by examiner

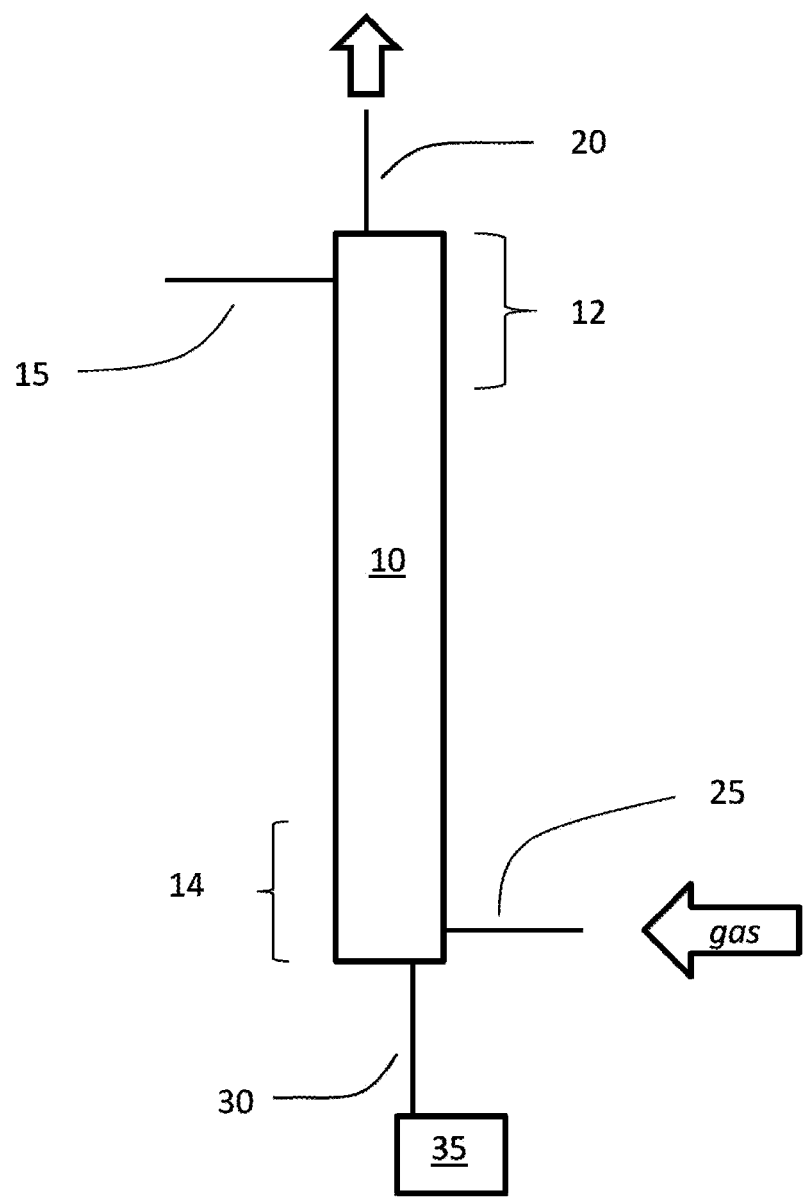

ORGANOMETALLIC COMPOUND PURIFICATION AND APPARATUS

This application claims the benefit of priority under 35 U.S.C. §119(e) to U.S. Provisional Application No. 61/507,334, filed Jul. 13, 2011, the entire contents of which application are incorporated herein by reference.

The present invention relates to the field of metal-containing compounds and particularly to the field of purifying metal-containing compounds.

Metal-containing compounds are used in a variety of applications, such as catalysts and sources for growing metal films. One use of such compounds is in the manufacture of electronic devices such as semiconductors. Many semi-conducting materials are manufactured using well-established deposition technologies that employ ultrapure metalorganic (organometallic) compounds, for example, metalorganic vapor phase epitaxy, metalorganic molecular beam epitaxy, metalorganic chemical vapor deposition and atomic layer deposition. To be useful in these processes the organometallic compounds must be free from contaminants and/or deleterious impurities. If not removed, such impurities present in the organometallic sources can cause adverse effects on the electronic and/or optoelectronic properties of electronic devices.

Crude organometallic compounds typically contain various impurities resulting from reaction byproducts, impurities in starting materials, residual solvent, or any combination of these. Such impurities are often very difficult to remove from the desired organometallic compound. Typical processes used to purify such crude organometallic compounds are distillation, sublimation, Soxhlet extraction, and crystallization.

U.S. Pat. No. 6,495,707 discloses a method of manufacturing trimethylgallium ("TMG") supposedly without the need for a separate purification step by adding both gallium trichloride and trimethylaluminum to the center of a reaction column, vaporizing the TMG produced and collecting the TMG from the top of the reaction column. However, the yields of TMG obtained from this process are low, only 50-68%, and the purity of the obtained TMG is not discussed.

Chinese published patent application CN 1872862 A discloses an improvement to the process of the U.S. Pat. No. 6,495,707 patent in which the vaporized TMG produced is conveyed from the reaction column to the bottom of a stripping column which has a topmost condenser section. The temperature of the stripping column is kept above the boiling point of the TMG. Nitrogen gas is also added to the bottom of the stripping column. As the nitrogen gas moves upward through the stripping column, it conveys vaporized TMG with it, and the portion of the TMG that does not condense in the condenser section exits the stripping column with the nitrogen stream from the top of the stripping column and is collected. This improved process still produces TMG in relatively low yields (59%). Although the TMG produced according to the CN 1872862 A application is disclosed to be 99.96% pure, this is still insufficient purity for many electronic applications.

There remains a need to provide organometallic compounds in very high purity.

The present invention provides a method of purifying an organometallic compound comprising: (a) providing a crude organometallic compound in a liquid phase; (b) providing a stripping column having a first portion with a first inlet and a first outlet and a second portion with a second inlet and a second outlet; (c) feeding the crude organometallic compound in the liquid phase to the first portion of the stripping column through the first inlet; (d) feeding a gas stream to the second portion of the stripping column through the second inlet; (e) directing the crude organometallic compound through the stripping column opposite to a flow of the gas stream; and (f) collecting purified organometallic compound in the liquid phase from the second outlet. The gas stream flows in opposite direction to the direction of the flow of the organometallic compound.

The present invention further provides an apparatus for continuously purifying an organometallic compound comprising: (a) a source of crude organometallic compound in a liquid phase; (b) a source of a stripping gas; (c) a stripping column having a first portion with a first inlet and a first outlet and a second portion with a second inlet and a second outlet; (d) the first inlet in fluid communication with the source of the crude organometallic compound; (e) the second inlet in fluid communication with the source of stripping gas; and (f) the second outlet being in fluid communication with a collector for purified organometallic compound; wherein a flow of the crude organometallic compound in the stripping column is opposite to a flow of the stripping gas in the stripping column. The first outlet provides an exit for the stripping gas from the stripping column.

FIG. 1 is a schematic depiction of a purification apparatus suitable for use with the process of the invention.

The articles "a" and "an" refer to the singular and the plural. Unless otherwise noted, all amounts are percentages by weight and all ratios are molar ratios. All numerical ranges are inclusive and combinable in any order except where it is clear that such numerical ranges are constrained to add up to 100%.

It will be understood that when an element is referred to as being "on" another element, it can be directly on the other element or intervening elements may be present therebetween. In contrast, when an element is referred to as being "directly on" or "immediately on" another element, there are no intervening elements present.

It will be understood that, although the terms first, second, third, and so forth may be used herein to describe various elements, components, regions, layers, portions or sections, these elements, components, regions, layers, portions or sections should not be limited by these terms. These terms are only used to distinguish one element, component, region, layer, portion or section from another element, component, region, layer, portion or section. Thus, a first element, component, region, layer, portion or section discussed below could be termed a second element, component, region, layer or section without departing from the teachings of the present invention.

Furthermore, relative terms, such as "lower" or "bottom" and "upper" or "top," may be used herein to describe one element's relationship to another element as may be illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

The term "cocurrent" refers to the flow of two fluids in the same direction. The term "countercurrent" refers to the flow of two fluids in opposing directions. "Fluid" refers to a gas, a liquid or a combination of a gas and a liquid. "Alkyl" includes straight chain, branched and cyclic alkyl. The terms "column" and "tower" are used interchangeably. "Halogen" refers to fluorine, chlorine, bromine and iodine. The following abbreviations shall have the following meanings: ppm=refers to parts per million; m=meters; mm=millimeters; kPa=kilopascals; hr=hours; and psi=pounds per square inch.

The present invention provides a method of purifying a crude organometallic compound. Crude organometallic compound in a liquid phase is conveyed to a stripping column having a first portion with a first inlet and a first outlet and a second portion with a second inlet and a second outlet. The crude liquid-phase organometallic compound is fed into the first portion of the stripping column through the first inlet. A gas stream is fed into the second portion of the stripping column through the second inlet. The crude organometallic compound is directed through the stripping column opposite to the flow of the gas stream, that is the liquid-phase organometallic compound and the gas stream have countercurrent flows. Purified organometallic compound is collected from the second outlet. The present process advantageously removes relatively more volatile impurities as compared to the organometallic compound to be purified. That is, the present process removes impurities having a relatively higher vapor pressure as compares to the organometallic compound to be purified.

FIG. 1 is a schematic diagram of an apparatus suitable for use with the process of the invention having stripping column 10 having a first portion 12 and a second portion 14. Stripping column 10 may optionally contain mass transfer devices, not shown. First portion 12 has a first inlet 15 and a first outlet 20. Second portion 14 has a second inlet 25 and a second outlet 30. Second outlet 30 is in fluid communication with collector 35 for receiving purified organometallic compound.

In operation, the crude organometallic compound in the liquid phase is conveyed into first portion 12 of stripping column 10 by way of first inlet 15 and is directed through stripping column 10 toward second portion 14 and exits the stripping column through second outlet 30. A gas stream is conveyed into the second portion 14 of stripping column 10 by way of second inlet 25 and is directed through stripping column 10 toward first portion 12 and exits the stripping column by way of first outlet 20. In the apparatus of FIG. 1, liquid-phase crude organometallic compound flows downward from first portion 12 toward second portion 14 while the gas flows upward from second portion 14 toward first portion 12. The liquid-phase crude organometallic compound and the gas have countercurrent flows. The organometallic compound collected in receiver 35 from second outlet 30 is purified as compared to the crude organometallic compound as it enters the stripping column though first inlet 15.

Stripping column 10 may be composed of any suitable material which will not react with the organometallic compound to be purified. Suitable materials include, without limitation: glass such as borosilicate glass and PYREX glass; plastics including perfluorinated plastics such as poly(tetrafluoroethylene); quartz; or metal. Metals are preferred, and particularly suitable metals include, without limitation, nickel alloys and stainless steels. Suitable stainless steels include, but are not limited to, 304, 304 L, 316, 316 L, 321, 347 and 430. Suitable nickel alloys include, but are not limited to, INCONEL, MONEL, and HASTELLOY corrosion-resistant alloys. The stripping column may be composed of a mixture of materials, such as glass-lined stainless steel. The choice of suitable material for the stripping column is well within the ability of those skilled in the art.

The dimensions of the stripping column are not critical, and the stripping column may have any suitable length and diameter. The choice of such length and diameter will depend on the volume of the crude organometallic compound to be purified, and the desired amount of contact between the liquid-phase crude organometallic compound and the inert gas, among other factors within the ability of those skilled in the art. Typical lengths range from 1 to 12 m, more preferably from 1.5 to 10 m, yet more preferably from 2 to 8 m, and even more preferably 2 to 5 m. Particularly preferred lengths are 1.5, 2, 3, 4, 5, 6, 7, 8 and 10 m. Typical diameters range from 10 mm to 3 m, preferably from 15 mm to 2 m, more preferably from 15 mm to 1 m, still more preferably from 15 to 500 mm, even more preferably from 15 mm to 250 mm, more preferably from 25 to 200 mm and yet more preferably from 25 to 150 mm. Particularly preferred diameters are 10, 15, 20, 25, 30, 35, 40, 50, 75 and 100 mm.

Optionally, stripping column 10 may include one or more heat transfer portions, not shown in FIG. 1. Such heat transfer portion may be present anywhere along stripping column 10. For example, the heat transfer portion may be part of first portion 12, second portion 14, or a part of both first and second portions. Such heat transfer portion includes heat exchangers such as condensers, chillers, and heaters. For example, a chiller may be employed to maintain the temperature of the column so that the organometallic compound remains in the liquid-phase. Alternatively, when the organometallic compound is a relatively low-melting solid, a heater may be employed to maintain the organometallic compound in the liquid-phase. The selection of a specific heat transfer portion, and its location in the stripping column, will depend on the size of the stripping column, the volume of crude organometallic compound to be purified, the temperature of the crude organometallic compound, the particular crude organometallic compound to be purified, the particular impurities, and quantities of impurities to be removed, among other factors known to those skilled in the art. Such selection of the heat transfer portion and its location in the stripping column is within the ability of one skilled in the art.

The stripping column may optionally contain any suitable mass transfer devices which will not react with the organometallic compound. Such mass transfer devices may be random packing, structured packing, trays or a combination thereof. The random packing material may be any of a wide variety of shapes, such as, but not limited to, baffles, beads, rods, tubes, horseshoes, plates, rings, saddles, discs, saucers, or any other suitable form such as aciform, cruciform, and helicoids (coils and spirals). Mixtures of shapes may be used. The size of the random packing material used will depend on a number of considerations, such as the size of the stripping column and the number of theoretical plates desired to separate impurities from the organometallic compound. Suitable random packing material may have a wide variety of sizes (e.g., diameters), such as 2 mm or greater. A suitable range of sizes for the random packing material is from 2 to 50 mm in diameter. Structured packing material includes wire gauze, corrugated plates, monolithic honeycombs, grids, and the like. The wire gauze may be woven or knitted and may be perforated and/or corrugated. Corrugated plates may optionally be perforated and/or textured. It is preferred that the structured packing is wire gauze. The packing material may be of a uniform size or may be a mixture of sizes. A wide variety of trays may optionally be used in the stripping column of the present invention. Exemplary trays include, without limitation, baffles, floating valves, fixed valves, sieve trays, dual flow trays, co-current flow tray, and the like. Determination of the type, size, quantity, and location of the mass transfer devices within the column are well within the ability of one skilled in the art. Mass transfer devices are generally commercially available from a variety of sources, such as Raschig, HAT International, Koch-Glitsch, ACS Separations and Sulzer Chemtech.

Mass transfer devices may be composed of any suitable material, or mixture of materials, that does not react with the organometallic compound to be purified. Exemplary materials useful in packing materials include, without limitation: ceramics such as alumina, silica, alumina silicates, silicon carbide, and silicon nitride; glass such as borosilicate glass; quartz; graphite balls such as Bucky balls; metals such as the stainless steels and nickel alloys described above, as well as titanium and zirconium; and thermoset plastics. Certain metals, such as nickel and chromium, are known to enhance the decomposition of Group 13 organometallic compounds and are best avoided when Group 13 organometallic compounds are purified. However, alloys containing nickel or chromium may be used when Group 13 organometallic compounds are purified.

The crude organometallic compound in the liquid-phase enters the first portion of the stripping column through the first inlet. Any crude organometallic compound which is in the liquid-phase may be suitably employed in the present process. Such organometallic compounds include compounds that are liquid at the temperatures employed during the purification step. For example, when the organometallic compound is a liquid, it may be purified according to the present process at any temperature above its freezing point and below its boiling point. Relatively-low melting point solid organometallic compounds may be purified in the liquid phase by appropriately heating the stripping column to a temperature above the melting point of the organometallic compound, but below its boiling point. When a liquid organometallic compound is to be purified according to the present process, it is preferable to heat the stripping column appropriately to prevent the organometallic compound from solidifying in the stripping column from evaporative cooling. Preferably, a liquid organometallic compound is purified at a temperature from 5° C. above its freezing point to 5° C. below its boiling point, and more preferably from 10° C. above its freezing point to 10° C. below its boiling point.

Organometallic compounds that are either solid or liquid at the temperature of the stripping column may be dissolved in a solvent to provide a liquid-phase organometallic compound which is then purified according to the present process. Any suitable organic solvent may be used. Any organic solvent may be used provided that it does not react with or destabilize the organometallic compound, and provided that the organic solvent has a vapor pressure that is less than the vapor pressure of the impurities to be removed. Suitable solvents are known to those skilled in the art. Preferred solvents include, but are not limited to: hydrocarbons such as linear alkyl benzenes, xylene, mesitylene, durene, quinoline, isoquinoline, indane, 1,2,3,4-tetrahydronaphthalene (tetralin), decahydronaphthalene and squalane; and ionic liquids. Ionic liquids are generally salts that are liquid at low temperatures, having melting points under 100° C. Ionic liquids are composed entirely of ions and typically they are composed of bulky organic cations and inorganic anions. Due to the high Coulumbic forces in these compounds, ionic liquids have practically no vapor pressure. Any suitable ionic liquid may be employed as the solvent in the present invention. Exemplary cations used in ionic liquids include, but are not limited to, hydrocarbylammonium cation, hydrocarbylphosphonium cation, hydrocarbylpyridinium cation, and dihydrocarbylimidazolium cation. Exemplary anions useful in the present ionic liquids include, without limitation: chlorometalate anion; fluoroborate anion such as tetrafluoroborate anion and hydrocarbyl substituted fluoroborate anion; and fluorophosphate anion such as hexafluorophosphate anion and hydrocarbyl substituted fluorophosphate anion. Exemplary chlorometalate anions include: chloroaluminate anion such as tetrachloroaluminate anion and chlorotrialkylaluminate anion; chlorogallate anions such as chlorotrimethylgallate; and tetrachlorogallate, chloroindate anions such as tetrachloroindate and chlorotrimethylindate.

Dissolving an organometallic compound in an organic solvent to provide a liquid-phase allows the present process to be used to purify an organometallic compound that may be difficult to purify otherwise. For example, trimethylindium melts at 88° C. and decomposes explosively at 101-103° C. This leaves a very small temperature range over which trimethylindium may be purified as a neat liquid without decomposing. However, trimethylindium is known to be stable in solution, such as in squalane, at temperatures >125° C. for prolonged periods. Dissolving trimethylindium in squalane allows for a greater range of temperatures to be employed in the stripping column in the preset process without decomposing the trimethylindium. Certain organometallic compounds are relatively high melting, such as dicyclopentadienyl magnesium which melts at 180° C., and may be difficult to purify as a melt according to the present process. Providing such relatively higher melting organometallic compounds in a solvent allows for the purification of such organometallic compounds in a liquid-phase according to the present process.

A wide variety of organometallic compounds may be purified by the present process. As used herein, "organometallic compound" refers to a compound having at least one metal-carbon, metal-oxygen, metal-nitrogen or metal-phosphorus bond. Suitable organometallic compounds contain at least one metal atom chosen from Group 2-Group 14, preferably from Group 3 to Group 14, and more preferably from Group 3 to Group 13. Particularly preferred metals are those in Groups 3, 4, 5, 8, 9, 10, 11 and 13, and even more preferably Groups 4, 8, 11 and 13. Exemplary metal atoms include, without limitation, magnesium, calcium, strontium, scandium, yttrium, lutetium, lawrencium, lanthanum, titanium, zirconium, hafnium, cerium, vanadium, niobium, tantalum, chromium, molybdenum, tungsten, manganese, ruthenium, cobalt, rhodium, iridium, nickel, platinum, palladium, copper, silver, gold, zinc, aluminum, gallium, indium, silicon, germanium, and tin. Preferred metal atoms include magnesium, strontium, scandium, yttrium, lutetium, lawrencium, titanium, zirconium, hafnium, vanadium, niobium, tantalum, molybdenum, tungsten, manganese, ruthenium, cobalt, iridium, nickel, platinum, palladium, copper, silver, gold, zinc, aluminum, gallium, indium, and germanium. It is more preferred that the metal atom is magnesium, scandium, yttrium, lutetium, lawrencium, titanium, zirconium, hafnium, niobium, tantalum, molybdenum, tungsten, ruthenium, cobalt, iridium, nickel, platinum, palladium, copper, silver, gold, aluminum, gallium, indium and germanium, and even more preferred are magnesium, zirconium, hafnium, niobium, tantalum, molybdenum, tungsten, ruthenium, cobalt, iridium, nickel, copper, aluminum, gallium, indium and germanium, and yet more preferred are magnesium, zirconium, hafnium, aluminum, gallium, indium and germanium.

Exemplary organometallic compounds are those of the formula $R_a M^m X_{m-a} L$ (formula I), where each R is independently chosen from $(C_1-C_{20})$alkyl, $(C_2-C_{20})$alkenyl, $(C_2-C_{20})$alkynyl, $(C_5-C_{20})$aryl, $(C_5C_{20})$aryl$(C_1-C_{10})$alkyl, $(C_1-C_{20})$alkoxy, $(C_2-C_{10})$carbalkoxy, amino, $(C_1-C_{12})$alkylamino$(C_1-C_{12})$alkyl, di$(C_1-C_{20})$alkylamino$(C_1-C_{12})$alkyl, phosphino, and a divalent ligand; each X is independently chosen from H, R, cyano, and halogen; L=a neutral ligand; a=the valence of the R group and is an integer≥1; M=a Group 2 to Group 14 metal; and m=the valence of M. The "amino" groups include —$NH_2$, $(C_1-C_{12})$alkylamino, and di$(C_1-C_{12})$alkylamino. Preferably, the amino groups are —$NH_2$, $(C_1-C_6)$alkylamino, and di$(C_1-C_6)$alkylamino, and more preferably —$NH_2$, $(C_1-C_4)$alkylamino, and di$(C_1-C_4)$alkylamino. "Phosphino" groups include —$PH_2$, $(C_1-C_{12})$alkylphosphino, and di$(C_1-C_{12})$alkylphosphino, preferably include —$PH_2$, $(C_1-C_6)$alkylphosphino, and di$(C_1-C_6)$alkylphosphino, and more preferably include —$PH_2$, $(C_1-C_4)$alkylphosphino, and di$(C_{1-C4})$alkylphosphino. The above R groups may optionally be substituted by replacing one or more hydrogen atoms with one or more substituent groups, such as halogen, carbonyl, hydroxyl, cyano, amino, alkylamino, dialkylamino, and alkoxy. For example, when R is a $(C_1-C_{20})$alkyl group, such group may contain a carbonyl within the alkyl chain. Suitable divalent ligands include, without limitation, β-diketonates, amidinates, formamidinates, phosphoamidinates, guanidinates, β-diketiminates, bicyclic amidinates and bicyclic guanidinates. Preferred divalent ligands include β-diketonates, amidinates, formamidinates, phosphoamidinates, and guanidinates. Depending on the particular metal atom, the organometallic compounds of formula II may optionally contain one or more neutral ligands (L). Such neutral ligands do not bear an overall charge. Neutral ligands include, without limitation, CO, NO, nitrogen, amines, ethers, phosphines, alkylphosphines, arylphosphines, nitriles, alkenes, dienes, trienes, alkynes, and aromatic compounds. Adducts of organometallic compounds of formula I with amines or phosphines, such as tertiary amines or tertiary phosphines, are contemplated by the present invention.

Preferably, each R group in formula I is independently selected from $(C_1-C_{10})$alkyl, $(C_2-C_{10})$alkenyl, $(C_2-C_{10})$alkynyl, $(C_5-C_{15})$aryl, $(C_5-C_{10})$aryl$(C_1-C_6)$alkyl, $(C_1-C_{10})$alkoxy, $(C_2-C_{10})$carbalkoxy, amino, $(C_1-C_6)$alkylamino$(C_1-C_6)$alkyl, di$(C_1-C_6)$alkylamino$(C_1-C_6)$alkyl, phosphino, and a divalent ligand; and more preferably $(C_1-C_6)$alkyl, $(C_2-C_6)$alkenyl, $(C_2-C_6)$alkynyl, $(C_5-C_{10})$aryl, $(C_5-C_8)$aryl$(C_1-C_6)$alkyl, $(C_1-C_6)$alkoxy, $(C_2-C_6)$carbalkoxy, amino, $(C_1-C_4)$alkylamino$(C_1-C_6)$alkyl, di$(C_1-C_4)$alkylamino$(C_1-C_6)$alkyl, phosphino, and a divalent ligand. It is further preferred that each R is independently selected from $(C_1-C_5)$alkyl, $(C_2-C_3)$alkenyl, $(C_2-C_3)$alkynyl, $(C_5-C_8)$aryl, $(C_5-C_8)$aryl$(C_1-C_4)$alkyl, $(C_1-C_5)$alkoxy, $(C_2-C_5)$carbalkoxy, amino, $(C_1-C_4)$alkylamino$(C_1-C_4)$alkyl, di$(C_1-C_4)$alkylamino$(C_1-C_4)$alkyl, phosphino, and a divalent ligand, and still more preferably $(C_1-C_4)$alkyl, $(C_2-C_3)$alkenyl, $(C_5-C_8)$aryl, $(C_1-C_5)$alkoxy, amino, $(C_1-C_3)$alkylamino$(C_1-C_4)$alkyl, di$(C_1-C_3)$alkylamino$(C_1-C_4)$alkyl, phosphino, and a divalent ligand.

Preferred organometallic compounds have the structure of formula II

$$R^1{}_xX^2{}_{n-x}M2^n \quad \text{(formula II)}$$

wherein each $R^1$ is independently chosen from $(C_1-C_6)$alkyl, $(C_2-C_6)$alkenyl, $(C_1-C_4)$alkylamino$(C_1-C_6)$alkyl, di$(C_1-C_4)$alkylamino$(C_1-C_6)$alkyl, $(C_5-C_{10})$aryl, —$NH_2$, $(C_1-C_4)$alkylamino, and di$(C_1-C_4)$alkylamino; each $X^2$ is independently chosen from H, halogen, $(C_1-C_{10})$alkoxy and $R^1$; M2 is a Group 2, 4 or 13 metal; x is the valence of the $R^1$ group and is an integer; n is the valence of M2; and $1 \le x \le n$. Adducts of organometallic compounds of formula II with amines or phosphines, such as tertiary amines or tertiary phosphines, are contemplated by the present invention. It is preferred that each $R^1$ is independently chosen from $(C_1-C_4)$alkyl, $(C_2-C_4)$alkenyl, $(C_5-C_{10})$aryl, —$NH_2$, $(C_1-C_4)$alkylamino, and di$(C_1-C_4)$alkylamino; and more preferably $(C_1-C_4)$alkyl, $(C_5-C_8)$aryl, —$NH_2$, $(C_1-C_4)$alkylamino, and di$(C_1-C_4)$alkylamino. Preferred groups for $R^1$ include, without limitation, methyl, ethyl, n-propyl, iso-propyl, butyl, tert-butyl, iso-butyl, sec-butyl, n-pentyl, iso-pentyl, neo-pentyl, vinyl, allyl, propargyl, aminomethyl, aminoethyl, aminopropyl, dimethylaminopropyl, methylamino, dimethylamino, ethylmethylamino phenyl, cyclopentadienyl, methylcyclopentadienyl, and pentamethylcyclopentadienyl. When $X^2$ is a halogen, chlorine and bromine are preferred and chlorine is more preferred. When M2 is a Group 2 metal, x=1 or 2. When M2 is a Group 4 metal, x=1, 2, 3 or 4. When M2=a Group 13 metal, x=1, 2 or 3. M2 is preferably magnesium, zirconium, hafnium, aluminum, indium or gallium, and more preferably aluminum, indium or gallium.

Preferred organometallic compounds include, but are not limited to: trialkyl indium compounds such as trimethyl indium, triethyl indium, tri-n-propyl indium, tri-iso-propyl indium, dimethyl iso-propyl indium, dimethyl ethyl indium, dimethyl tert-butyl indium, methyl di-tert-butyl indium, methyl di-isopropyl indium, and tri-tertiarybutyl indium; trialkyl indium-amine adducts such as trialkyl indium-tertiaryamine adducts; dialkyl haloindium compounds such as dimethyl indium chloride; alkyl dihaloindium compounds such as methyl dichloroindium; cyclopentadienyl indium; trialkyl indium-trialkyl-phosphine adducts such as trimethyl indium-trimethyl phosphine adduct; trialkyl gallium compounds such as trimethyl gallium, triethyl gallium, tri-iso-propyl gallium, tri-tert-butyl gallium, dimethyl iso-propyl gallium, diethyl tert-butyl gallium, methyl di-iso-propyl gallium, dimethyl tert-butyl gallium, dimethyl neo-pentyl gallium, and methyl ethyl iso-propyl gallium; trialkyl gallium-amine adducts such as trialkyl gallium-tertiary amine adducts; trialkyl gallium-phosphine adducts; alkyl dihalogallium compounds such as methyl dichlorogallium, ethyl dichlorogallium and methyl dibromogallium; dialkyl halogallium compounds such as dimethyl gallium chloride and diethyl gallium chloride; trialkylaluminum compounds such as trimethyl aluminum, triethyl aluminum, tri-n-propyl aluminum, tri-iso-propyl aluminum, tri-tert-butyl aluminum, dimethyl iso-propyl aluminum, dimethyl ethyl aluminum, dimethyl tert-butyl aluminum, methyl di-tert-butyl aluminum, and methyl di-iso-propyl aluminum; trialkylaluminum-amine adducts such as trialkylaluminum-tertiaryamine adducts; diaklyl haloaluminum compounds such as dimethyl aluminum chloride and diethylaluminum chloride; alkyl dihaloaluminum compounds such as methyl aluminum dichloride, ethyl aluminum dichloride, and ethyl aluminum dibromide; dicyclopentadienyl magnesium; metal dialkylamido compounds such as tetrakis(ethylmethylamino) zirconium and tetrakis(ethylmethylamino) hafnium; metal beta-diketonates such as beta-diketonates of hafnium, zirconium, tantalum and titanium; and metal amidinates such as amidinates of copper, lanthanum, ruthenium, and cobalt. Such organometallic compounds are generally commercially available or may be prepared by a variety of procedures known in the art. For example, Group 13 organometallic compounds may be prepared by methods described in, for example, U.S. Pat. Nos. 5,756,786; 6,680,397; and 6,770,769. Metal amidinate compounds may be prepared by methods described in, for example, U.S. Pat. Nos. 7,638,645; and 7,816,550.

The gas stream is conveyed into the second portion of the stripping column by way of the second inlet and is directed through the stripping column toward the first portion and exits the stripping column by way of the first outlet. The flow of the gas stream is counter to the flow of the organometallic compound. Optionally, the gas may be heated. A variety of gas flow rates may be used, and are easily determined by one skilled in the art. The flowing inert gas entrains or otherwise removes volatile impurities from the organometallic compound and carries such volatile impurities with it as it exits the stripping column through the first outlet. Preferably, the gas is inert. Any gas that is inert to the organometallic compound may be used in the present invention. Exemplary inert gases include, without limitation, nitrogen, argon, helium, methane, ethane, propane, and $CO_2$. It will be appreciated by those skilled in the art that $CO_2$ may not be suitable for use with every organometallic compound as it may form a complex with certain organometallic compounds. Such $CO_2$ complexes are well known to those skilled in the art.

The organometallic compound flows from the first portion toward the second portion of the stripping column while the inert gas flows in an opposing (countercurrent) direction countercurrent. The organometallic compound, which exits the stripping column through the second outlet, is purified as compared to the organometallic compound entering the stripping column at the first inlet. As used herein, "purified organometallic compound" refers to an organometallic compound where relatively more volatile impurities have been removed. Purified organometallic compound obtained from the present process has a reduced or greatly eliminated amount of relatively more volatile impurities. As used herein, "relatively more volatile" refers to impurities having a higher vapor pressure that the organometallic compound under the conditions used in the stripping column. For example, when the organometallic compound is an organoaluminum compound, particularly an alkylaluminum compound, such as a dialkylaluminum halide or a trialkylaluminum, relatively more volatile silicon-containing impurities are removed by the present process. It is preferred that purified organoaluminum compounds are substantially free of silicon-containing impurities. "Substantially free" means that the purified organometallic compound contains less than 5 ppm of a specific impurity, preferably less than 3 ppm, more preferably less than 2 ppm, even more preferably less than 1 ppm, and yet more preferably ≤0.5 ppm of such impurity. Preferably, the purified organometallic compound contains ≤0.5 ppm of metallic impurities chosen from silicon, germanium and tin.

As the present process removes relatively more volatile impurities, the purified organometallic compound obtained from the present process may be further purified as needed, such as to remove relatively less volatile impurities. The term "relatively less volatile" refers to impurities having a lower vapor pressure than the organometallic compound to be purified. Any conventional technique for further purification of the organometallic compound may be used, including, for example, distillation or sublimation. Such further purification techniques are well-known in the art.

The countercurrent flows of organometallic compound and the gas stream through the stripping column provide a process for continuous purification of a crude organometallic compound. However, the present process may also be used in a batch purification process.

The purified organometallic compounds of the present invention may be used in a variety of applications that demand the use of high purity organometallic compounds, such as in certain catalyst applications and in the manufacture of electronic devices such as light emitting diodes. The present purified organometallic compounds may also be used as intermediates in the preparation of other organometallic compounds.

EXAMPLE 1

The following table illustrates various organometallic compounds to be purified according to the present process. Suitable organic solvents are listed where such solvents are needed.

| Compound | Melting Point (° C.) | Boiling Point (° C.) | Solvent |
|---|---|---|---|
| $(CH_3)_3Ga$ | −15 | 56 | None or LAB |
| $(CH_3)_3In$ | 88 | 101-103* | Squalane |
| $(CH_3)_3Al$ | 15 | 125 | None |
| $(CH_3CH_2)_3Ga$ | −82 | 109 | None |
| $(CH_3CH_2)_3In$ | −32 | 184 | None |
| $(CH_3CH_2)_3Al$ | −46 | 128 | None |
| $(CH_3CH_2)_2GaCl$ | <10 | 60-62 @ 2 mm Hg | None |
| $(CH_3)_2AlCl$ | −21 | 127 | None |
| $(CH_3)_2InCl$ | 218-219 | — | Indane |
| TDMAHf | 26-29 | 85 @ 0.1 mm | None |
| TDMAZr | 57-60 | 80 @ 0.1 mm | None |
| TEMAHf | <−20 | — | None |
| TEMAZr | <−20 | — | None |
| $Cp_2Mg$ | 180 | 290 | Squalane |

The abbreviations have the following meanings: LAB=linear alkyl benzenes; Cp=cyclopentadienyl; TDMA=tetrakis(dimethylamino) or $[(CH_3)_2N]_4$; and TEMA=tetrakis(ethylmethylamino) or $[(CH_3)(CH_3CH_2)N]_4$.

EXAMPLE 2

A stream consisting of trimethylaluminum-tripropylamine adduct ("TMA-TPA") with a slight excess of tripropylamine was fed at a rate of 42 units/hr and at a temperature of 136° C. to the top section of a packed stripping tower equipped with an integral condenser. A nitrogen gas stream at a flow rate of 2 units/hr at ambient temperature conditions was countercurrently flowed into the bottom of the stripping tower. The stripping tower pressure was controlled at a pressure of 7-14 kPa (1-2 psi) greater than atmospheric pressure and the condenser operated to result in the exiting gas stream having a temperature of 65-75° C. The stripping tower was run predominately continuously for more than 24 hours and yielded a liquid TMA-TPA stream that was reduced in concentration of measureable volatile hydrocarbons and contained less than 0.5 ppm of silicon-containing impurities. Greater than 90% removal efficiency of relatively more volatile impurities was achieved.

EXAMPLE 3

The procedure of Example 2 is repeated except that TMA-TPA is replaced by TEMAZr and helium is used as the gas stream. The temperature of the stripping tower is maintained so that the TEMAZr remains liquid.

EXAMPLE 4

The procedure of Example 2 is repeated except that TMA-TPA is replaced by $(CH_3)_3Ga$ dissolved in LAB. The temperature of the stripping tower is maintained at ≤110° C.

EXAMPLE 5

The procedure of Example 3 is repeated except that TEMAZr is replaced by TDMAHf. The temperature of the stripping tower is maintained at ≥40° C.

EXAMPLE 6

The procedure of Example 2 is repeated except that TMA-TPA is replaced by $(CH_3)_3In$ dissolved in squalane, helium is used as the gas, and the temperature of the stripping tower is maintained at ≤120°, and preferably ≤100° C.

EXAMPLE 7

The procedure of Example 4 is repeated except that the $(CH_3)_3Ga$ dissolved in LAB is replaced by $Cp_2Mg$ dissolved in squalane and methane is used as the gas. The temperature of the stripping tower is maintained at ≤175° C.

What is claimed is:

1. A method of continuously purifying an organometallic compound comprising: (a) providing a crude organometallic compound in a liquid phase; (b) providing a stripping column having a first portion with a first inlet and a first outlet and a second portion with a second inlet and a second outlet; (c) feeding the crude organometallic compound in the liquid phase to the first portion of the stripping column through the first inlet; (d) feeding an inert gas stream to the second portion of the stripping column through the second inlet; (e) directing the crude organometallic compound through the stripping column opposite to a flow of the inert gas stream; and (f) collecting organometallic compound in the liquid phase from the second outlet, wherein the collected organometallic compound is purified as compared to the crude organometallic compound as it enters the stripping column.

2. The method of claim 1 wherein the crude organometallic compound of step (a) is dissolved in an organic solvent.

3. The method of claim 1 wherein the crude organometallic compound comprises one or more metal atoms chosen from magnesium, zirconium, hafnium, aluminum, gallium, indium, and germanium.

4. The method of claim 1 wherein the crude organometallic compound has the formula $R_a M^m X_{m-a} L$, wherein each R is independently chosen from $(C_1-C_{20})$alkyl, $(C_2-C_{20})$alkenyl, $(C_2-C_{20})$alkynyl, $(C_5-C_{20})$aryl, $(C_5-C_{20})$aryl$(C_1-C_{10})$alkyl, $(C_1-C_{20})$alkoxy, $(C_2-C_{10})$carbalkoxy, amino, $(C_1-C_{12})$alkylamino$(C_1-C_{12})$alkyl, di$(C_1-C_{20})$alkylamino$(C_1-C_{12})$alkyl, phosphino, and a divalent ligand; each X is independently chosen from H, R, cyano, and halogen; L=a neutral ligand; a=the valence of the R group and is an integer≥1; M=a Group 2 to Group 14 metal; and m=the valence of M.

5. The method of claim 4 wherein the crude organometallic compound has the formula $R^1_x X^2_{n-x} M2^n$, wherein each $R^1$ is independently chosen from $(C_1-C_6)$alkyl, $(C_2-C_6)$alkenyl, $(C_1-C_4)$alkylamino$(C_1-C_6)$alkyl, di$(C_1-C_4)$alkylamino$(C_1-C_6)$alkyl, $(C_5-C_{10})$aryl, $-NH_2$, $(C_1-C_4)$alkylamino, and di$(C_1-C_4)$alkylamino; each $X^2$ is independently chosen from H, halogen, $(C_1-C_{10})$alkoxy and $R^1$; M2 is a Group 2, 4 or 13 metal; x is the valence of the $R^1$ group and is an integer; n is the valence of M2; and 1≤x≤n.

6. The method of claim 1 wherein the crude organometallic compound is heated in step (a).

7. The method of claim 1 wherein the purified organometallic compound contains ≤0.5 ppm of metallic impurities chosen from silicon, germanium and tin.

8. The method of claim 1 wherein the inert gas stream is chosen from nitrogen, argon, helium, methane, ethane, propane, and $CO_2$.

9. The method of claim 1 wherein the stripping column further comprises a heat transfer zone.

10. The method of claim 1 wherein the stripping column further comprises mass transfer devices.

11. The method of claim 10 wherein the mass transfer devices are chosen from random packing, structured packing, trays and combinations thereof.

12. The method of claim 1 wherein the crude organometallic compound flows downward from the first portion toward the second portion while the inert gas flows upward from the second portion toward the first portion.

* * * * *